(12) United States Patent
Hasson et al.

(10) Patent No.: US 10,045,541 B2
(45) Date of Patent: Aug. 14, 2018

(54) ANTI-MICROBIAL COMPOSITION

(71) Applicant: SULTAN QABOOS UNIVERSITY, Al Khodh (OM)

(72) Inventors: Sidgi Syed Anwer Abdo Hasson, Muscat (OM); Ali A. H. Al-Jabri, Muscat (OM); Khazina Al-Harthy, Muscat (OM)

(73) Assignee: SULTAN QABOOS UNIVERSITY, Al Khodh (OM)

( * ) Notice: Subject to any disclaimer, the term of this patent is extended or adjusted under 35 U.S.C. 154(b) by 0 days.

(21) Appl. No.: 15/617,995

(22) Filed: Jun. 8, 2017

(65) Prior Publication Data

US 2018/0103648 A1    Apr. 19, 2018

Related U.S. Application Data (60) Provisional application No. 62/410,375, filed on Oct. 19, 2016.

(51) Int. Cl.

| | |
|---|---|
| *A01N 65/12* | (2009.01) |
| *A01N 65/08* | (2009.01) |
| *A61K 36/285* | (2006.01) |
| *A61K 36/185* | (2006.01) |
| *A61K 9/00* | (2006.01) |
| *A61K 9/10* | (2006.01) |
| *A61K 9/68* | (2006.01) |
| *A61K 9/14* | (2006.01) |
| *A61K 8/97* | (2017.01) |
| *A61Q 11/00* | (2006.01) |

(52) U.S. Cl.
CPC ............. *A01N 65/12* (2013.01); *A01N 65/08* (2013.01); *A61K 8/97* (2013.01); *A61K 9/0053* (2013.01); *A61K 9/0058* (2013.01); *A61K 9/10* (2013.01); *A61K 9/14* (2013.01); *A61K 36/185* (2013.01); *A61K 36/285* (2013.01); *A61Q 11/00* (2013.01)

(58) Field of Classification Search
CPC ......... A61K 35/78; A61K 36/185; A61K 8/97
USPC .................................... 424/769, 734
See application file for complete search history.

(56) References Cited

U.S. PATENT DOCUMENTS

| | | | |
|---|---|---|---|
| 2003/0228383 A1 * | 12/2003 | Doshi | A61K 36/00 424/734 |
| 2008/0057111 A1 | 3/2008 | Jiang et al. | |
| 2009/0175971 A1 * | 7/2009 | Dreher | A61K 36/185 424/769 |
| 2009/0191288 A1 | 7/2009 | Squires et al. | |

FOREIGN PATENT DOCUMENTS

| | | | | |
|---|---|---|---|---|
| CN | 102091306 | * | 6/2011 | ......... A61K 36/9068 |

OTHER PUBLICATIONS

Uniprot, "Taxonomy-Saussurea costus (Costus) (Aucklandia costus)." www.uniprot.org/taxonomy/324593; published online Aug. 3, 2008. (Year: 2008).*

* cited by examiner

*Primary Examiner* — Walter E Webb
(74) *Attorney, Agent, or Firm* — Richard C. Litman (57) ABSTRACT

An anti-microbial composition includes an extract of at least one of *Aucklandia lappa* Decne and *Punica granatum*. The extract can be an aqueous ethanol extract. The extract can be formed using the peel of the pomegranate and the root of the *Aucklandia lappa* Decne. A weight ratio of the *Aucklandia lappa* Decne and *Punica granatum* in the composition can range from about 4:1 to about 1:1.

15 Claims, 8 Drawing Sheets

ANTI-MICROBIAL COMPOSITION

CROSS REFERENCE TO RELATED APPLICATION

This application claims the benefit of U.S. Provisional Patent Application Ser. No. 62/410,375, filed Oct. 19, 2016.

BACKGROUND OF THE INVENTION

Field of the Invention

The present invention relates generally to anti-microbial compositions, and particularly to anti-microbial compositions including extracts of *Aucklandia lappa* Decne and *Punica granatum*.

Description of the Related Art

Chronic pharyngitis is an inflammation of pharyngeal mucosal tissue leading to swallowing difficulties, throat irritation, such as itching, dryness, or pain in throat, dry cough, nausea, and/or vomiting when brushing teeth. A variety of factors can induce chronic pharyngitis, including, repeated episodes of acute pharyngitis, upper respiratory tract disease, changes in climate and geographical environment, temperature, humidity, poor air quality, tobacco and alcohol stimulation, spicy food, dust, harmful gases, radioactive radiation, and/or systemic factors. Traditionally, clinicians have mainly used antibiotics and/or anti-inflammatory medications to control microbial infections and inflammation associated with chronic pharyngitis. These drugs typically have an unpleasant taste, are prematurely discontinued by patients, and have other complications.

Thus, an anti-microbial composition for treating chronic pharyngitis and oral cavity infection solving the aforementioned problems is desired.

SUMMARY OF THE INVENTION

An anti-microbial composition includes an extract of at least one of *Aucklandia lappa* Decne (herein, "AID") and *Punica granatum* (herein, pomegranate or "Pgp"). The extract can be a total alcohol, essential oil, or aqueous extract. For example, the extract can be an aqueous ethanol extract. The extract can be formed using the peel of the pomegranate and the root of the AID. A weight ratio of the AID to pomegranate in the composition can range from about 4:1 to about 1:1.

A method of treating a patient suffering from a microbial infection includes administering to a patient in need thereof a therapeutically effective amount of an anti-microbial composition including an ethanolic aqueous extract of *Aucklandia lappa* Decne and/or *Punica granatum*.

These and other features of the present invention will become readily apparent upon further review of the following specification and drawings.

DETAILED DESCRIPTION OF THE PREFERRED EMBODIMENTS

An anti-microbial composition includes an extract of at least one of Aucklandia Lappa Decne (herein, "AID") and *Punica granatum* (herein, "pomegranate" or "Pgp"). The extract can be a total alcohol, essential oil or aqueous extract. For example, the extract can be an aqueous ethanol extract. The extract can be formed using the peel of the pomegranate and the root of the AID. A weight ratio of the AID and pomegranate in the composition can range from about 4:1 to about 1:1.

A method of treating a patient suffering from an oral or nasal infection can include administering to a patient in need thereof a therapeutically effective amount of the anti-microbial composition. The anti-microbial composition can include an ethanolic aqueous extract of *Aucklandia lappa* Decne and/or *Punica granatum*. The anti-microbial composition can be used to treat bacterial, fungal, and/or viral infections of the throat, skin, oral cavity, nasal cavity, and/or ear cavity. The anti-microbial composition can be used for disinfecting surfaces and wounds, and/or for personal hygiene. The composition can be formulated as a chewing gum, sachet filling, mouthwash, toothpaste, pastilles, lozenges, boiled sweets, ointment, jellies, lotions and powders. The composition can be formulated as a hand wrap jell, soap, and/or shampoo for clinical and/or personal hygienic uses.

A therapeutically effective amount of *Aucklandia lappa* Decne and *Punica granatum* to treat infections of the throat or oral cavity can be from about 0.5 mg to about 2 mg of AID and from about 0.4 mg to about 1.0 mg of Pgp. For example, a therapeutically effective amount of the AID per chewing gum piece can be from about 0.8 mg to about 1.8 mg or from about 1 mg to about 1.5 mg or about 1.2 mg per gum piece. A therapeutically effective amount of the Pgp can be per chewing gum piece can be from about 0.1 mg to about 1.0 mg or from about 0.3 mg to about 0.8 mg, or from about 0.5 mg to about 0.7 mg per gum piece. When both AID and Pgp are present in the composition, then the AID to Pgp ratio can range from about 2:1 to about 1:1 or from about 4:1 to about 1:1.

A method of preparing a chewing gum composition including *Aucklandia lappa* Decne and/or *Punica granatum* peel as an active antiseptic agent includes admixing a therapeutically effective amount of the anti-microbial composition including *Aucklandia lappa* Decne and/or *Punica granatum* with a chewing gum base; and compressing the composition with the gum base to obtain a compressed chewing gum unit. The chewing gum composition might be an acidulated chewing gum or a non-acidulated chewing gum. A non-acidulated chewing gum is favored. The composition may have an undesirable taste. Accordingly, a taste covering agent can be included in the chewing gum composition. Such taste masking may include, but shall not be limited to, compounds for example, menthol or peppermint oil. On the other hand or in addition, the chewing gum composition may include a natural or artificial sweetener. Such sweeteners may include, but are not be restricted to aspartame, polyol sweeteners, such as, (crystalline) xylitol, sorbitol (which is also an excellent humectant and texturizing agent), mannitol and erythritol. Examples of some usually available sweeteners include, but are not limited to, sucrose, lactose, dextrose, maltose, dextrin, dried inverted sugar, fructose, levulose, galactose, corn syrup, hydrogenated starch hydrolysates, maltitol, sucralose, aspartame, salts of acesulfame potassium, alitame, saccharin and its salts, cyclamic acid and its salts, glycyrrhizin, dihydrochalcones, thaumatin, monellin, and so forth, and alternatively mixtures thereof. The amount of sweetener present in the chewing gum composition may change contingent on, inter alia, the nature of the sweetener. Generally an amount of sweetener ranging from about 1 to 5% w/w or from about 1 to 3% w/w is preferred.

The gum base can include natural latex, vegetable gum, Arabian gum and/or mastic gum. The gum base can be present in an amount ranging from about 8% to about 25% w/w of the chewing gum. The gum may further include a sugar, artificial sweetener, or wax coating. The chewing gum composition may further include at least one of a flavoring agent, softening agent, coloring agent, filler and an artificial sweetener. One or more coloring agents, such as natural food dyes or artificial colorings, such as Fast green (E143), Allura red (E129), brilliant blue (E133), Erythrosine (pink)(E127), tartrazine (E102), sunset yellow (E1 10) and indigotine (E132) can be included. Waxes may likewise be utilized as helpful softening agents include natural and synthetic waxes, hydrogenated vegetable oils, petroleum waxes for example, paraffin waxes, microcrystalline waxes polyurethane waxes, polyethylene waxes, mixtures thereof, and so on which may be incorporated into the gum base.

As used herein, a therapeutically effective amount of the *Aucklandia lappa* Decne extract and *Punica granatum* extract or an amount effective to treat or prevent an oral infection may be determined initially from in vivo studies described herein. For example, an effective amount of the anti-microbial composition can be about 20 mg/ml to about 250 mg/ml.

The present technology, thus generally described, will be understood more readily by reference to the following examples, which are provided by way of illustration.

EXAMPLE 1

Preparation of Ethanolic Extract Formulation of the Anti-microbial Composition

The root of *Aucklandia lappa* Decne and the peel of *Punica granatum* were weighed, thoroughly washed in de-ionized water to remove any dirt, soil, undesirable contaminants, and allowed to dry in an oven overnight. The root and peel were then ground in a ratio of 56 g *Aucklandia lappa* Decne and 28 g of *Punica granatum* peel into a powdered state. The powder was mixed with 96% ethanol to form a mixture. The mixture was allowed to be incubated for 72 hours at room temperature and then filtered to separate the residue debris from the solution. The filtered solution was incubated in a water bath at 85° C. overnight to reduce the volume to ¼ of the original quantity as well as to evaporate the remaining ethanol solvent. A solid form object formed during the heating period was removed by second filtration using Whatman filter paper-1M. The concentration of the "filtered" solution was then adjusted and weighed accordingly. The extract obtained was a dark brown aqueous extract.

EXAMPLE 2

In-Vitro Analyses

Common pathogenic bacteria, e.g., *Streptococcus pyogenes* bacteria, were used to test the antimicrobial activity of the anti-microbial composition. Examination was also conducted for the composition against methicillin-resistant *S. aureus* (MRSA), multi-drug resistant *Acinetobacter baumanii*, ESBL *E. coli, K. pneumonia*, which are routinely isolated, identified and tested for antibiotic susceptibility in the Microbiology Diagnostic Laboratory, Sultan Qaboos University Hospital, Muscat, Oman.

The organisms should be in the log phase of growth in order for the results to be valid. Therefore, fresh cultures (3 to 4 hours cultures) were used. All Gram-negative bacteria were sub-cultured on Muller Hinton Blood agar media and incubated at 37° C. for 24 hours. All Gram-positive bacteria were sub-cultured on Blood agar and incubated at 37° C. for 24 hours. Each of the bacterial isolates used in this study was preserved in 2 mL of human blood at −80° C. till ready to use.

The antimicrobial activity of the *Aucklandia lappa* Decne and *Punica granatum* peel herbal composition extract was determined by the well diffusion method according to the Clinical Laboratory Standards Institute. Five different human bacteria isolates were tested, a) *Streptococcus pyogenes*, b) ESBL *E. coli*, c) *S. aureus*, d) *Acinetobacter*, and e) *K. pneumonia* for their inhibition by the anti-microbial composition. Mueller-Hinton agar media were inoculated with 24 hours cultures of bacterial suspensions (0.5 McFarland). Holes were made in the agar media by using 5 mm cork borer. Each hole was filled with 50 μL different dilution of a stock of 40 mg/mL anti-microbial composition, i.e., neat, ⅒, ¹/₁₀₀, and ¹/₁₀₀₀ dilutions. Media were incubated in a refrigerator for one hour for proper diffusion then incubated at 37° C. for 24 hours. Different antibiotics (Gentamicine 10 mg and Colistine CT 10 mg) were used appropriately as positive and negative controls. The antibacterial activity was assessed by measuring the inhibition zone diameter (mm) around each well and the mean of triplicate result was taken.

Figure 1A:
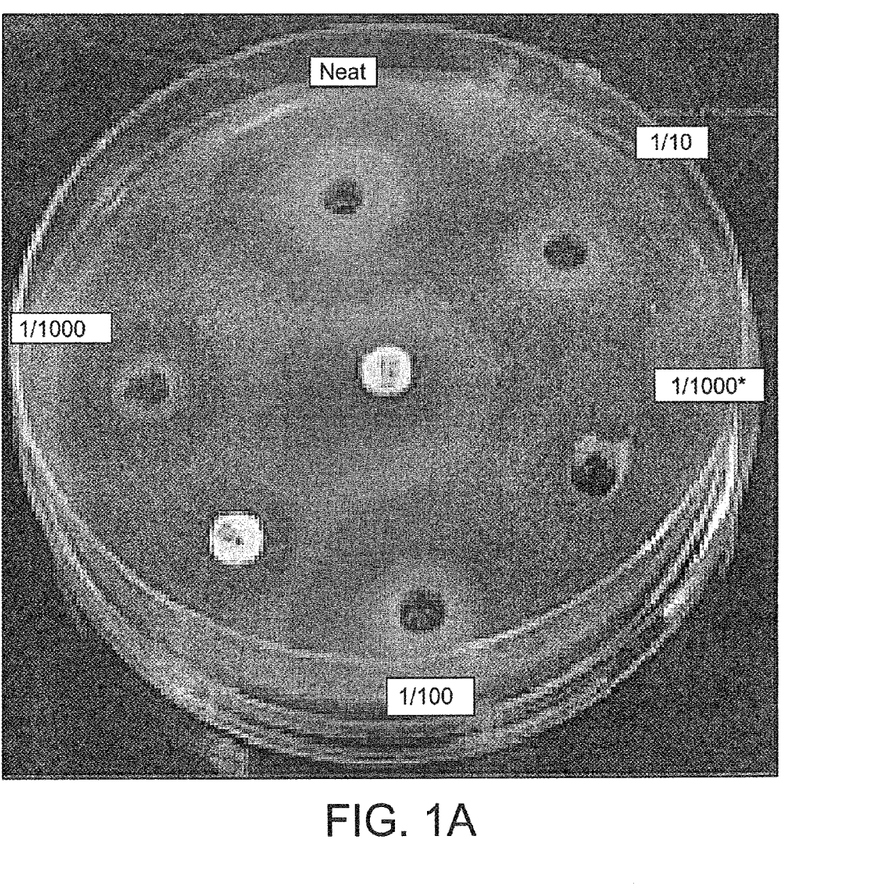
FIG. 1A is an image depicting the antibacterial assay including the anti-microbial composition contacted with *Streptococcus pyogenes* (*S. pyogenes*) using the well diffusion method.
Figure 1B:
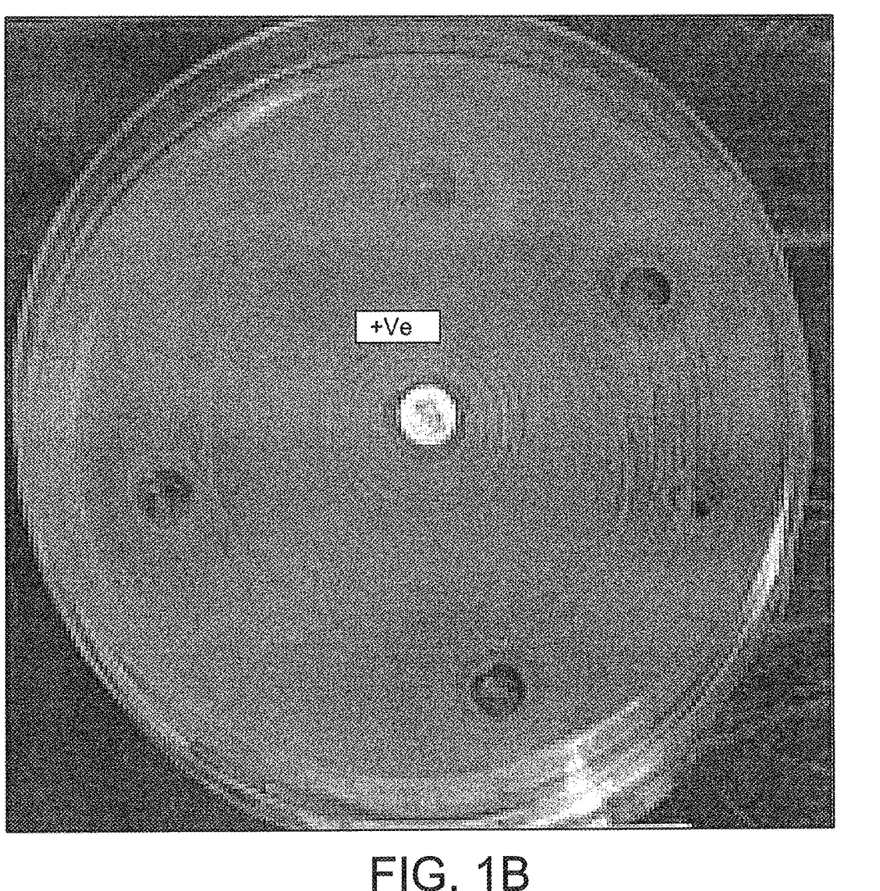
FIG. 1B is an image depicting the antibacterial assay including the anti-microbial composition contacted with Extended Spectrum Beta-Lactamases (ESBLs)—*Escherichia coli* (*E.coli*) (ESBL *E. coli*) using the well diffusion method.
Figure 1C:
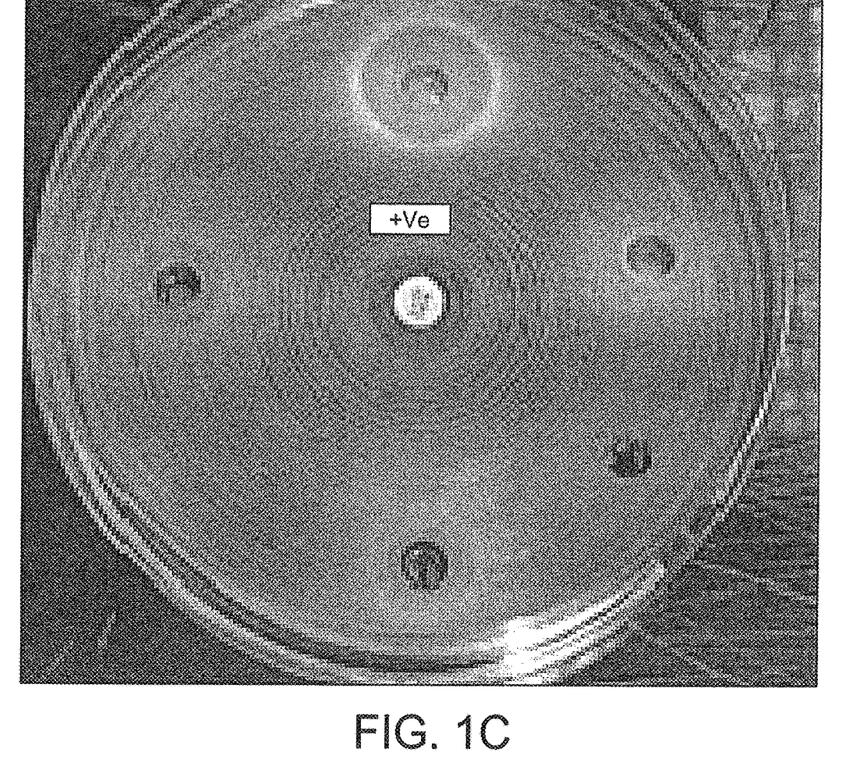
FIG. 1C is an image depicting the antibacterial assay including the anti-microbial compositions contacted with *Staphylococcus aureus* (*S. aureus*) using the well diffusion method.
Figure 1D:
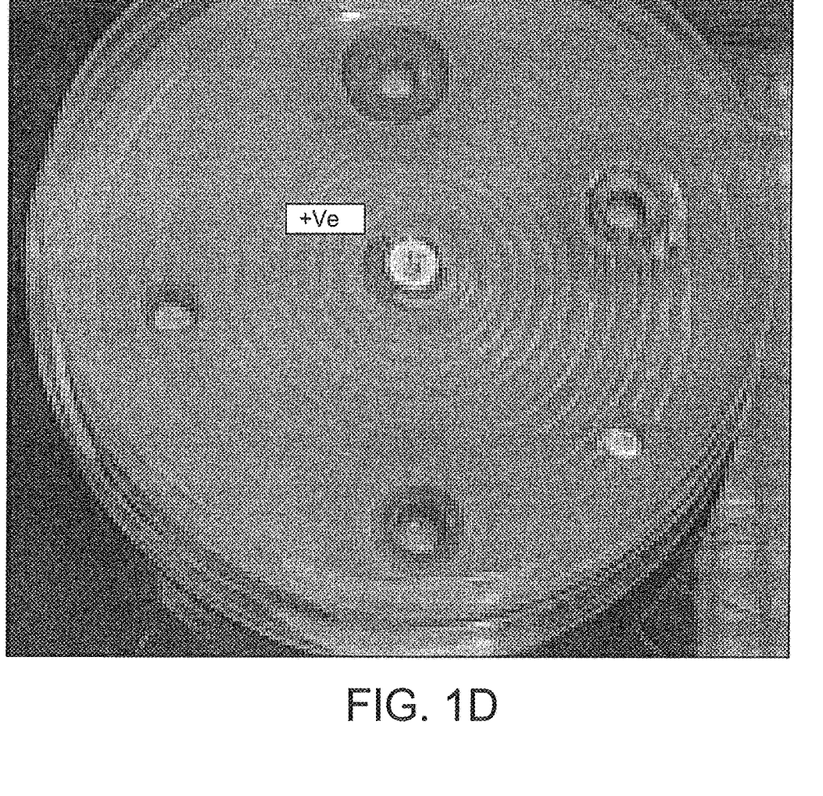
FIG. 1D is an image depicting the antibacterial assay of the anti-microbial compositions contacted with *Acinetobacter baumanii* using the well diffusion method.
Figure 1E:
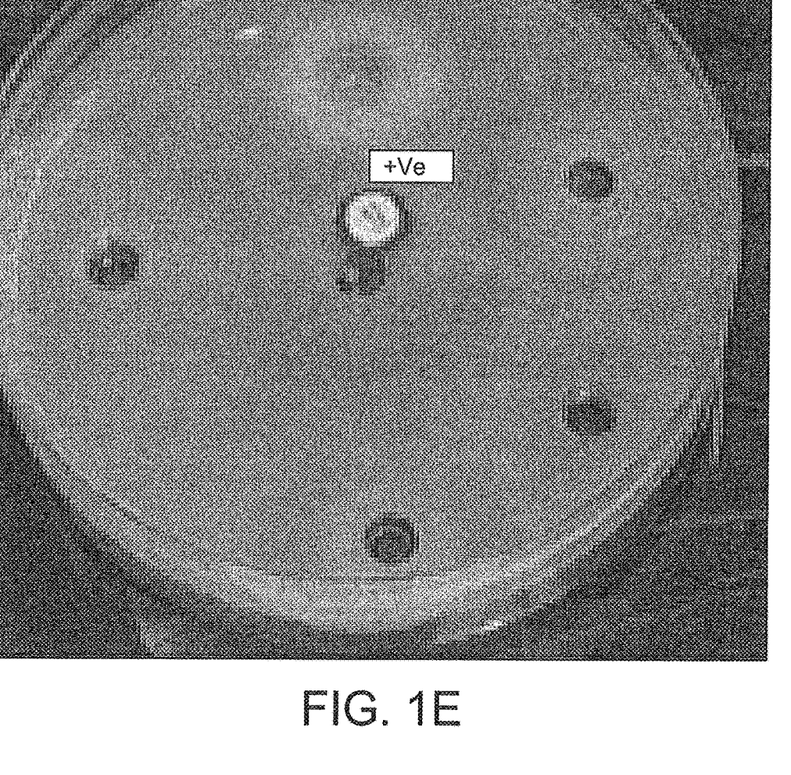
FIG. 1E is an image depicting the antibacterial assay of the anti-microbial compositions contacted with *Klebsiella pneumoniae* (*K. pneumoniae*) using the well diffusion method.

FIGS. 1A-1E show the antibacterial inhibition activity testing results for *Streptococcus pyrogens* (FIG. 1A), ESBL *E. coli* (FIG. 1B), *S. aureus* (FIG. 1C), *Acinetobacter baumanii* (FIG. 1D), and *K. pneumonia* (FIG. 1E). The results demonstrated that regardless of the different dilutions of the stock of 40 mg/ml anti-microbial composition used, all tested bacteria strains were significantly inhibited with variable inhibition zones in contrast to the positive antibiotic used as a control.

EXAMPLE 3

Disinfectant Activity Assay

The disinfectant activity of the anti-microbial composition was compared with the activity of two of the best common disinfectants agents available in the market and used with no dilution. Different concentrations of the anti-microbial composition were used, starting with the lower concentration that were used in the Well Diffusion Method, i.e., 20 mg/ml, 40 mg/ml, 80 mg/ml 120 mg/ml, 200 mg/ml, 250 mg/ml. Briefly sterile swabs were used, moistened with two disinfectants in parallel. A positive control included only sterile water. In general the swab was used to wipe a specific area on one of the laboratory benches. Furthermore, the control was used to wipe some areas prior to applying the disinfectants and the invented herbal composition. This was to make sure that the bacterial growth shown by using the control is from all areas allocated to wipe with the disinfectants and the herbal composition. After 1, 6 and 12 hours, respectively of wiping the allocated areas with the disinfectant and the anti-microbial composition a sterile swab was used to wipe the designated areas and inoculated using Colombia blood agar plates.

Figure 2A:
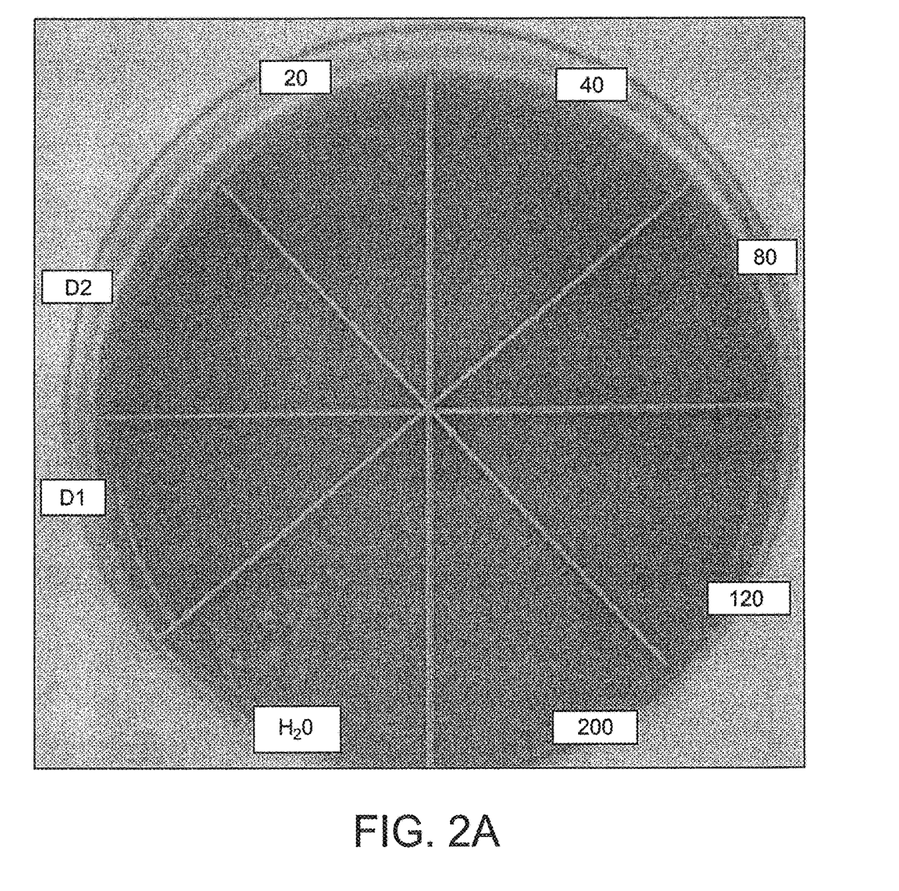
FIG. 2A is an image depicting the disinfectant activity assay after 1 hour of wiping the allocated area with disinfectants of various concentrations 20-200 mg/ml.
Figure 2B:
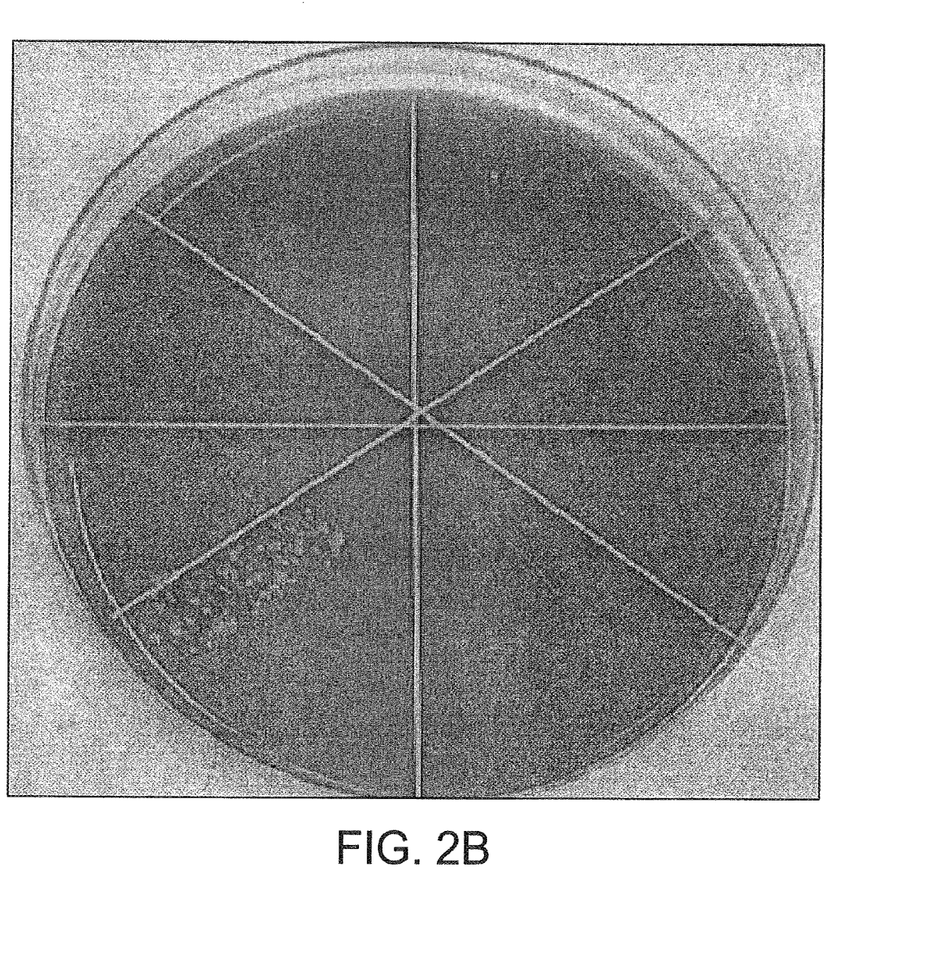
FIG. 2B is an image depicting the disinfectant activity assay after 6 hours of wiping the allocated area with disinfectants of various concentrations 20-200 mg/ml.
Figure 2C:
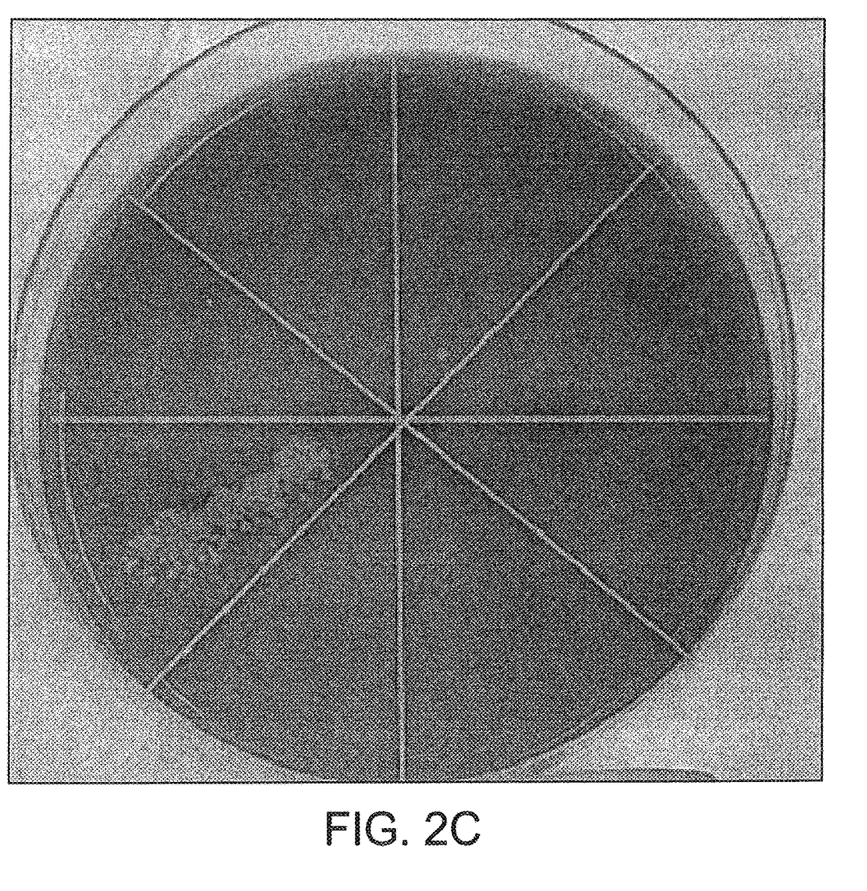
FIG. 2C is an image depicting the disinfectant activity assay after 12 hours of wiping the allocated area with disinfectants of various concentrations 20-200 mg/ml.

FIGS. 2A-2C, show the disinfectant assay after 1 hour, 6 hours, and 12 hours, respectively, of wiping the designated areas with Disinfectants D1 and D2 in parallel with the anti-microbial composition. The anti-microbial composition was found to significantly inhibit bacterial growth and inhibition increased with the concentration of herbal composition used. Regardless of the concentrations used, the anti-microbial composition was more effective than the best common disinfectants available in the market.

EXAMPLE 4

Toxicity Study of the Anti-microbial Composition in Animals

One of the essential early steps in product development includes the prediction and determination of its toxicity, i.e., "drug toxicity". Acute toxicity of the anti-microbial composition during oral administration in animals was examined. Rabbits (group-A) and WKY rats (group-B) were used in the toxicity profile. Group-A rabbits included twenty four (24) rabbits, including (16) males and (8) females, each weighing between 600 g to 1200 g. Group-B WKY rats included nineteen (19) WKY rats, including (11) males and (8) females, each weighing between 300 g to 600 g. Both the rabbits and the rats were randomly divided to investigate the lethal dosage. The anti-microbial composition as prepared above in Example 1 was given orally using antistatic at variable dosages to reach the optimum of 16 g/Kg for each animal group. The concentration of each dosage fluid containing the anti-microbial composition was about 1 g/ml. So the higher dosage group at 15 g/kg had a volume of about 5 ml, which could be calibrated to an adult human weighing sixty (60) kg who consumed 125 ml of the anti-microbial composition at a time. The animals were observed for behavior continuously for a period of two (2) weeks after such administration. Observation was conducted hourly at day 1. During the following days, observation was conducted four to six (4-6) times per day. At the end of the observation period, animals were sacrificed and dissected to examine the eyes, liver, lung, and spleen for adverse effects.

No abnormal behavior was observed for both groups of animals [i.e., the rabbits and rats] during the observation period. All animals (rabbits and rats) were alive after the two weeks of receiving the lethal dosage of 16 g/Kg. The rabbits and rats showed normal body weight increase during the two weeks period. Biochemical analysis showed normal range of ALT, AST, CBC, and GGT. Inspection of the eyes, liver, lung, and spleen (after scarification and dissection) showed no extraordinary signs. The results when compared to a general acute toxicity index were normal and no acute toxicity was observed. From that therefore, the weight ratio of the anti-microbial composition is preferred to be about 1-15 g/Kg.

EXAMPLE 5

Chewing Gum Preparation Including the Anti-microbial Composition

Uncoated chewing gum pieces (about 1 g each) were coated with a sucrose solution (80 % w/v) in a coating pan. Powdered, hydrogenated castor oil was scattered onto the coated chicle pieces and a coating of the anti-microbial composition was applied. Successive applications of the coating were made until approximately 1.2 mg of AID and 0.6 mg of Pgp were deposited on each chicle piece. A complete coating of a sucrose solution was applied containing desired flavorings and colorings. A polishing coat of wax was, alternatively, included.

EXAMPLE 6

Clinical Trial

A clinical trial was conducted as follows. Subjects were qualified to partake if they were otherwise healthy, had at least moderate manifestation severity and report side effects and/or symptoms of 48 hours or less duration. Symptoms are sore throat symptoms, in particular, pain, dryness and/or inflammation of the throat. The trial was blinded.

Subjects were haphazardly assigned to receive coated chewing gum pieces (about 1 g each) or a placebo chewing gum. The subject chewed on a gum piece every 1 to 3 hours from about 10 a.m. to 8 p.m. Subjects were instructed to avoid other cold, flu or sore throat medications while participating in the study.

Five adult humans, i.e., two females and three males, participated in this pre-clinical study. The study was a randomized, placebo-controlled clinical trial, which was alternatively blinded or two-fold blinded.

Before the first chewing gum was administered, baseline symptom side effect assessments were made utilizing an indication of symptom severity scale of 0 to 5, representing absent, mild, moderate, moderately severe, and severe symptoms, respectively. The side effects and/or symptoms rated are overall throat symptom assessment, sore throat, cough; overall nasal symptom assessment, sneezing, runny nose, nasal obstruction; overall sinus symptom assessment, sinus pain, sinus pressure, sinus congestion; headache, muscle pain, and disquietude. These manifestation assessments were made by the subjects in view of their self-impression of side effect and/or symptom type and location. Subjects also recorded the occurrence of any adverse effect. Subjects additionally recorded the event of any antagonistic impact. Every subject reported his or her indication evaluation after 12 to 48 hours. Study diaries were returned and reviewed.

The chewing gum composition that was utilized in this trial was made out of regular or natural wax mixed gum base with the anti-microbial composition, and no sweetener was used.

All participants found that their symptoms, i.e., pain, discomfort and moderate inflammation of sore throat were relieved within a period of 6 to 18 hours of taking the anti-microbial composition in the form of chewing gum.

EXAMPLE 7

Anti-microbial Composition Sachet Formulation

There is also provided a method for forming cold & flu relief decongestant sachets to relieve symptoms of colds and flu, including headache, aches and pains, sore throat, and nasal congestion, as hereinbefore described.

The sachet included approximately 1.2 mg of AID and 0.6 mg of Pgp. For direct use preparation, the sachet contents were emptied in a cup of 125 ml boiled water and left for 5 minutes prior oral intake.

Six adult humans, i.e., five females and one male, participated in this pre-clinical study. The study was a randomized, placebo-controlled clinical trial, which was optionally blinded or double-blinded. Subjects experienced chills, muscle ache, and/or running nose. Before the first chewing gum piece was administered, baseline symptom side effect assessments were made utilizing an indication of symptom severity scale of 0 to 5, representing absent, mild, moderate, moderately severe, and severe symptoms, respectively. The side effects and/or symptoms rated are overall throat symptom assessment, chills, muscle ache, and/or running nose. These manifestation assessments were made by the subjects in view of their self-impression of side effect and/or symptom type and location. Subjects also recorded the occurrence of any adverse effect. Subjects additionally recorded the event of any antagonistic impact. Every subject reported his or her indication evaluation after 12 to 48 hours. Study diaries were returned and reviewed.

All participants found that their symptoms, i.e., runny nose, muscle ache pain, nausea and discomfort were relieved within a period of 4 to 12 hours of taking the anti-microbial composition in sachets.

EXAMPLE 8

Anti-microbial Composition Mouthwash Formulation

A therapeutically active amount of the anti-microbial composition was prepared as a mouthwash "gargle" solution. The composition was used as a gargling solution several times a day. When used as a gargling solution, the anti-microbial composition was highly effective to treat pharyngitis, to reduce swelling in the throat, and loosen mucus, helping to flush out irritants or bacteria and eliminate bad breath.

The mouthwash "gargling" solution was prepared by mixing 10 g of the Aucklandia lappa Decne (AID) with 5 g Punica granatum peel (Pgp). The mixture was dissolved in 1% ethanol and 99% of water for a total volume suspension of 100 ml. The total volume of 50 ml suspension was enough for two-mouth washes so up scaling was necessary. All symptoms were found to disappear within 24 hours of taking the mouthwash four times to six times a day.

Nine adult humans, i.e., seven females and two males, participated in this pre-clinical study. The study was a randomized, placebo-controlled clinical trial, which was optionally blinded or double-blinded. Subjects experienced moderate sore throat, swallowing difficulties, nausea, and moderate increase in body temperature. Before the first chewing gum piece was administered, baseline symptom side effect assessments were made utilizing an indication of symptom severity scale of 0 to 5, representing absent, mild, moderate, moderately severe, and severe symptoms, respectively. The side effects and/or symptoms rated were overall throat symptom assessment, moderate sore throat, discomfort to swallow, nausea and moderate increase in body temperature. These manifestation assessments were made by the subjects in view of their self-impression of side effects and/or symptom type and location. Subjects also recorded the occurrence of any adverse effect. Subjects additionally recorded the event of any antagonistic impact. Every subject reported his or her indication evaluation after 12 to 48 hours. Study diaries were returned and reviewed.

All participants found that their symptoms, as stated above, of moderate sore throat, discomfort to swallow, nausea and moderate increase in their body temperature were relieved within a period of 9 to 36 hours of taking the anti-microbial composition in a form of gargling solution. Two of the female participants experienced vomiting after two to three hours due to undesirable taste. But they continued with some difficulty until their nausea symptoms were relieved.

Thus, as illustrated above, the anti-microbial composition can be used to relieve pain and/or discomfort associated with a chronic, mild or severe sore throat and/or oral cavity infections.

It is to be understood that the present invention is not limited to the embodiments described above, but encompasses any and all embodiments within the scope of the following claims.

We claim:

1. An anti-microbial composition consisting essentially of an extract of *Aucklandia lappa* Decne root extract and *Punica granatum* peel extract, wherein the weight ratio of the *Aucklandia lappa* Decne root extract and *Punica granatum* peel extract is from about 4:1 to about 1:1.

2. A method of treating a microbial infection comprising administering to a patient in need thereof a therapeutically effective amount of the composition according to claim 1.

3. The method according to claim 2, wherein the microbial infection includes a microbial infection of at least one of the throat, skin, oral cavity, nasal cavity, and ear cavity.

4. The method according to claim 3, wherein the therapeutically effective amount of the extract of *Aucklandia lappa* Decne and *Punica granatum* is a concentration of about 20 mg/ml to about 250 mg/ml.

5. The method according to claim 3, wherein the oral cavity infection is pharyngitis or tonsillitis.

6. The method according to claim 3, wherein the extract comprises *Aucklandia lappa* Decne root extract and *Punica granatum* peel extract and a weight ratio of the *Aucklandia lappa* Decne root extract and the *Punica granatum* peel extract is from about 4:1 to about 1:1.

7. The method according to claim 3, wherein the composition is administered orally and the composition is a liquid suspension.

8. The method according to claim 3, wherein the composition is a chewing gum.

9. The method according to claim 3, wherein the composition is a mouthwash.

10. The method according to claim 3, wherein the composition is in powder form.

11. A method of disinfecting a surface comprising contacting the surface with an amount of the anti-microbial composition of claim 1.

12. A method of preparing an anti-microbial chewing gum, comprising:
   admixing a therapeutically effective amount of the anti-microbial composition of claim 1 with a chewing gum base; and
   compressing the anti-microbial composition with the gum base to obtain a compressed chewing gum unit.

13. The method of preparing an anti-microbial chewing gum according to claim 12, wherein the gum base is selected from the group consisting of natural latex, vegetable gum, Arabian gum and mastic gum.

14. The method of preparing an anti-microbial chewing gum according to claim 13, wherein the gum base is present in an amount ranging from about 8% w/w to about 25% w/w of the chewing gum.

15. The method of preparing an anti-microbial chewing gum according to claim 13, wherein a gum piece includes about 1.2 mg of *Aucklandia lappa* Decne (AID) and about 0.6 mg of *Punica granatum*.

\* \* \* \* \*